(12) United States Patent
Ishitsu et al.

(10) Patent No.: US 10,292,669 B2
(45) Date of Patent: May 21, 2019

(54) RADIATION IMAGING APPARATUS, RADIATION COUNTING APPARATUS, AND RADIATION IMAGING METHOD

(71) Applicant: HITACHI, LTD., Tokyo (JP)

(72) Inventors: Takafumi Ishitsu, Tokyo (JP); Isao Takahashi, Tokyo (JP); Kazuma Yokoi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 15/560,291

(22) PCT Filed: Mar. 18, 2016

(86) PCT No.: PCT/JP2016/058725
§ 371 (c)(1),
(2) Date: Sep. 21, 2017

(87) PCT Pub. No.: WO2016/158501
PCT Pub. Date: Oct. 6, 2016

(65) Prior Publication Data
US 2018/0049707 A1 Feb. 22, 2018

(30) Foreign Application Priority Data
Mar. 30, 2015 (JP) .................. 2015-070281

(51) Int. Cl.
*G01T 1/17* (2006.01)
*A61B 6/00* (2006.01)
(Continued)

(52) U.S. Cl.
CPC ............ *A61B 6/4241* (2013.01); *A61B 6/032* (2013.01); *A61B 6/4258* (2013.01);
(Continued)

(58) Field of Classification Search
CPC .. G01T 1/17; G01T 1/172; G01T 1/36; A61B 6/4241; A61B 6/032; A61B 6/4258; A61B 6/4291
See application file for complete search history.

(56) References Cited

U.S. PATENT DOCUMENTS

2006/0086913 A1    4/2006  Spahn
2008/0099689 A1*   5/2008  Nygard ................. G01T 1/2018
                                                            250/370.09
(Continued)

FOREIGN PATENT DOCUMENTS

JP    2006-105995 A    4/2006
JP    2008-089384 A    4/2008
(Continued)

OTHER PUBLICATIONS

International Search Report of PCT/JP2016/058725 dated Apr. 19, 2016.

*Primary Examiner* — Michael C Bryant
(74) *Attorney, Agent, or Firm* — Mattingly & Malur, PC

(57) ABSTRACT

To improve performance in Photon Counting CT, pixel miniaturization, a reduction in circuit dead time, and dealing with scattered radiation and charge sharing are important. In addition, because the number of circuits increases, a reduction in power consumption of each circuit is important. Under these constraints, circuitry that deals with the scattered radiation is provided. Each pixel includes a circuit that determines whether radiation has been detected by another, adjacent pixel at the same time, and counters that count the radiation are switched on the basis of the result of the determination. On the basis of this result, counts of non-coincident events are primarily used, and coincident counts are used after being corrected, for reconstruction data.

13 Claims, 8 Drawing Sheets

(51) Int. Cl.
 *G01T 1/172* (2006.01)
 *G01T 1/36* (2006.01)
 *A61B 6/03* (2006.01)

(52) U.S. Cl.
 CPC .............. *A61B 6/4291* (2013.01); *G01T 1/17* (2013.01); *G01T 1/172* (2013.01); *G01T 1/36* (2013.01); *A61B 6/037* (2013.01); *A61B 6/4233* (2013.01)

(56) References Cited

U.S. PATENT DOCUMENTS

| | | | | |
|---|---|---|---|---|
| 2012/0305786 | A1* | 12/2012 | Dierickx | G01J 1/44 250/371 |
| 2013/0028382 | A1* | 1/2013 | Spahn | H04N 5/32 378/62 |
| 2013/0105701 | A1 | 5/2013 | Han et al. | |
| 2014/0321610 | A1* | 10/2014 | Ueki | G01T 1/2002 378/19 |
| 2015/0198725 | A1* | 7/2015 | Tamura | G01N 23/046 378/5 |

FOREIGN PATENT DOCUMENTS

| | | |
|---|---|---|
| JP | 2013-096993 A | 5/2013 |
| WO | 2013/089154 A | 6/2013 |

* cited by examiner

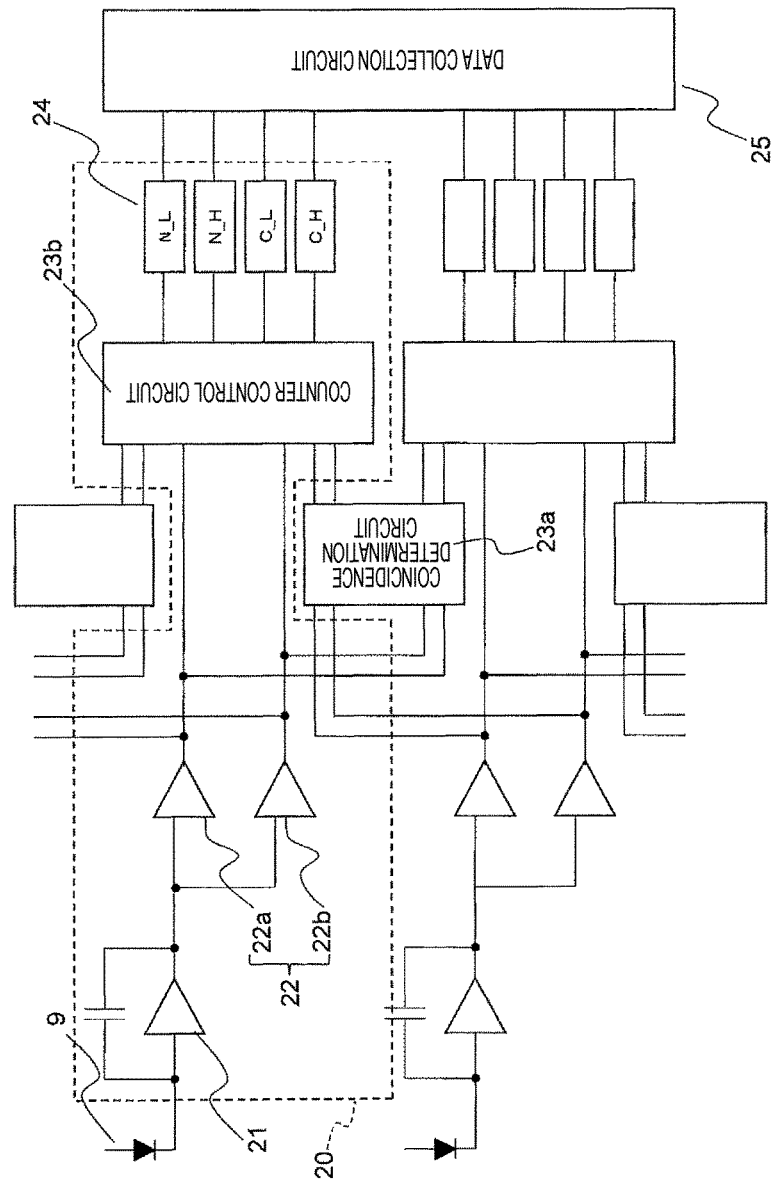

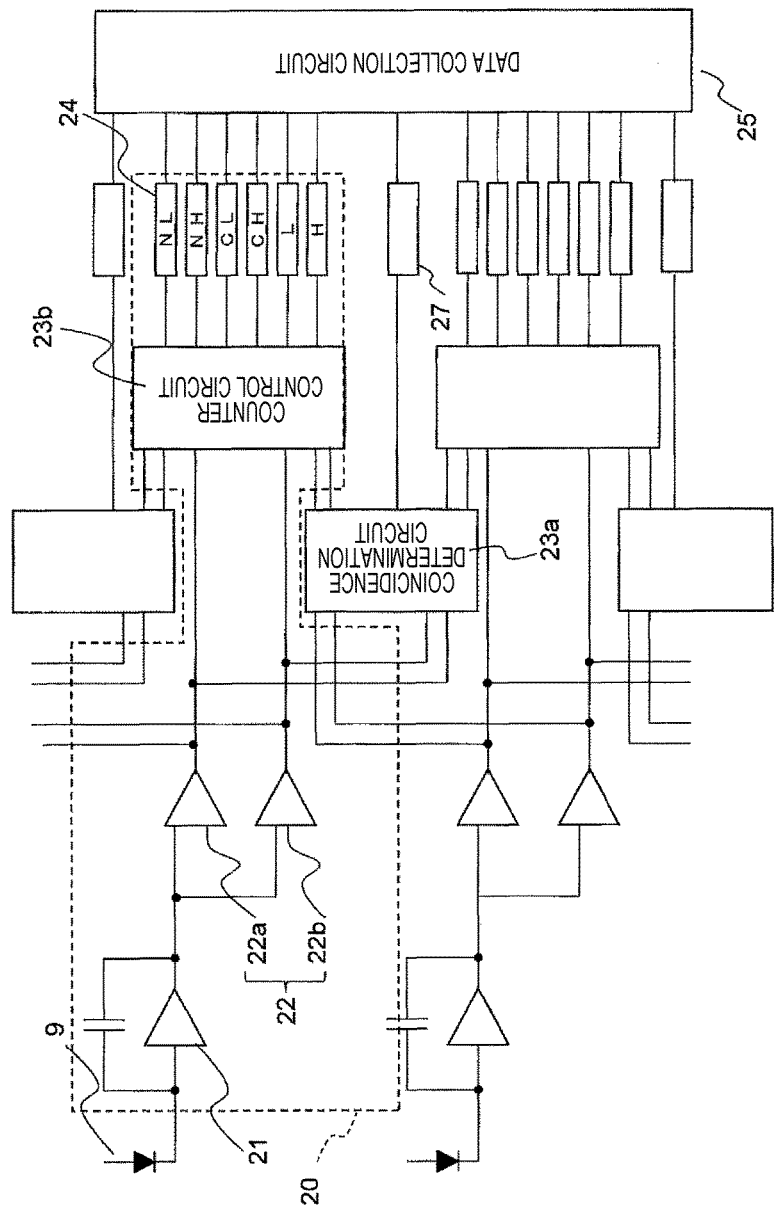

RADIATION IMAGING APPARATUS, RADIATION COUNTING APPARATUS, AND RADIATION IMAGING METHOD

TECHNICAL FIELD

The present invention relates to a radiation imaging apparatus and the like for reconstructing an image on the basis of a count value of radiation.

BACKGROUND ART

X-ray CT apparatuses are for obtaining a tomographic image of a subject from attenuation when X-rays generated from an X-ray tube pass through the body of the subject, and a technique called photon counting has been proposed to distinguish and detect energy of individual X-rays at each pixel of a detector.

In imaging by X-rays, the number of radiation generation is larger than that of inspection for nuclear medicine etc., and a counting rate in a detector is high. For this reason, it is necessary to lower the counting rate per pixel by downsizing detector pixels. In ordinary X-ray CT detectors, detectors are arranged at a pitch of about 1 mm. In photon counting CT which counts the number of photons, however, it is necessary to miniaturize detectors to a pitch of 0.5 mm to 0.05 mm. However, when detector pixels are miniaturized, phenomena such as detection of X-rays divided to a plurality of detector pixels due to occurrence of characteristic X-rays, Compton scattering, or the like or charge sharing where an electron cloud generated by X-rays spreads over two pixels occur at the time of X-ray detection. When these phenomena occur, an event originally to be detected as one high energy is observed as two low energy events. Since such erroneous detection deteriorates an image, erroneous detection has to be removed.

As a method of detecting such erroneous detection, there is a method of processing scattered radiation in a detector as described in PTL 1. By such a method, it is possible to process divided signals in the detector.

CITATION LIST

Patent Literature

PTL 1: Japanese Unexamined Patent Application Publication No. 2008-89384

SUMMARY OF INVENTION

Technical Problem

However, PTL 1 relates to positron emission computed tomography (PET), and when the incident rate of radiation is higher than that of PET like X-ray CT, processing takes time and dead time increases.

Also, in the case of a semiconductor detector used for X-ray CT, since pixels are formed by electrode division, there arises a problem that induced charges are temporarily generated in adjacent pixels during signal detection. Therefore, in the conventional method of adding peaks, there arises a problem that a signal higher than the original value is detected.

In view of the problems of the prior art as described above, it is an object of the present invention to provide a radiation imaging apparatus and the like capable of more appropriately counting radiation (photons).

Solution to Problem

In order to solve the above problems, each pixel monitors detectors (pixels) adjacent thereto, determines whether counting is performed coincidentally in the adjacent detectors, and by using data with higher energy acquires data for image reconstruction. More specifically, a radiation imaging apparatus, includes: a radiation detector including a plurality of detector pixels for detecting radiation; an energy measuring circuit for measuring energy when one of the detector pixels detects radiation on the basis of a signal output by the radiation detector; a plurality of counters for counting the number of detected radiations; a coincidence determination circuit for determining whether radiation has been coincidentally detected at other detector pixels adjacent to the detector pixel upon detection of the radiation; a counter control circuit for controlling operation of incrementing one of the counters on the basis of the coincidence determination in the coincidence determination circuit and the energy in the energy measuring circuit; and a data processing device for performing image reconstruction using values of the counters.

Means for solving other problems will be clarified by referring to drawings in embodiments of the invention to be described later.

Advantageous Effects of Invention

According to the present invention, a radiation imaging apparatus or the like capable of more appropriately counting radiation (photons) can be provided.

BRIEF DESCRIPTION OF DRAWINGS

FIG. 8 is a diagram illustrating a configuration of a circuit of a second embodiment of the present invention.

FIG. 9 is a diagram illustrating a configuration of a circuit of a third embodiment of the present invention.

DESCRIPTION OF EMBODIMENTS

Embodiments of a radiation imaging apparatus of the present invention and scattered radiation determination in a radiation counting apparatus (hereinafter referred to as "embodiments") will be described below with reference to the drawings. A radiation imaging method will also be described.

First Embodiment

Figure 1:
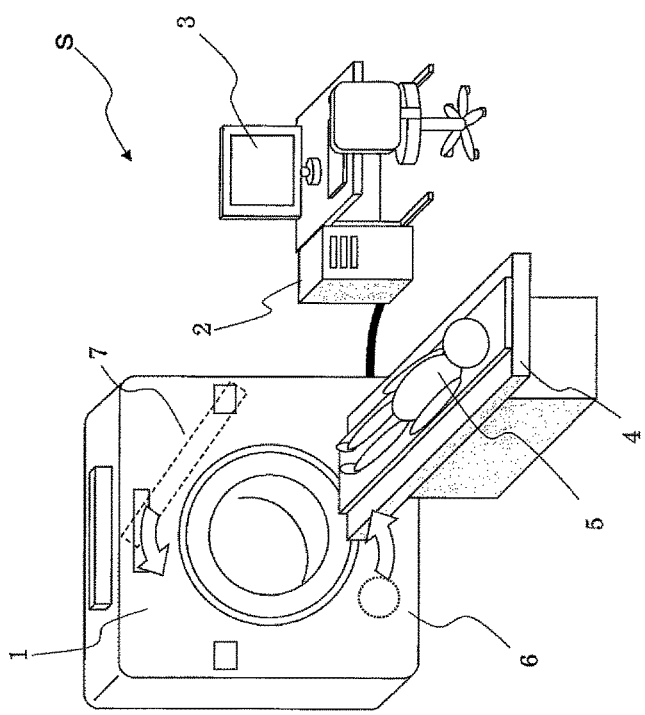
FIG. 1 is a diagram illustrating an exemplary apparatus of a first embodiment of the present invention.

A radiation imaging apparatus, a radiation counting apparatus, and a radiation imaging method (scattered radiation processing method considering scattered radiation in a detector) according to a first embodiment of the present invention will be described with reference to FIGS. 1 to 7. FIG. 1 is a diagram illustrating an example of an X-ray CT apparatus S which is an apparatus of the present embodiment.

As illustrated in FIG. 1, the X-ray CT apparatus (photon counting X-ray CT apparatus) S of the present embodiment includes a gantry 1, a data processing device 2 for processing collected data and reconstructing an image, and an image display device 3 for displaying the processed image. A bed 4 is attached to the gantry 1 and holds a subject 5. The bed 4 moves horizontally toward an opening of the gantry 1 and moves the subject 5 into the gantry 1.

In the gantry 1, an X-ray tube 6 and a detector panel 7 are arranged to face each other. The X-ray tube 6 and the detector panel 7 rotate about 1 to 3 times per second around the subject 5 while facing each other and acquire projection images of the subject 5 from respective directions. The X-ray tube 6 accelerates electrons with a high voltage of about 100 kV. X-rays are generated by accelerating electrons by a high electric field and hitting the target with the electrons. The generated X-rays pass through the subject 5 and reach the detector panel 7. At this time, the intensity of the X-rays is attenuated by the subject 5, so by knowing the amount of attenuation, information in the body can be acquired. In order to know a difference in attenuation due to energy, the voltage of the X-ray tube and a current for controlling a generated amount are changed.

Figure 2:
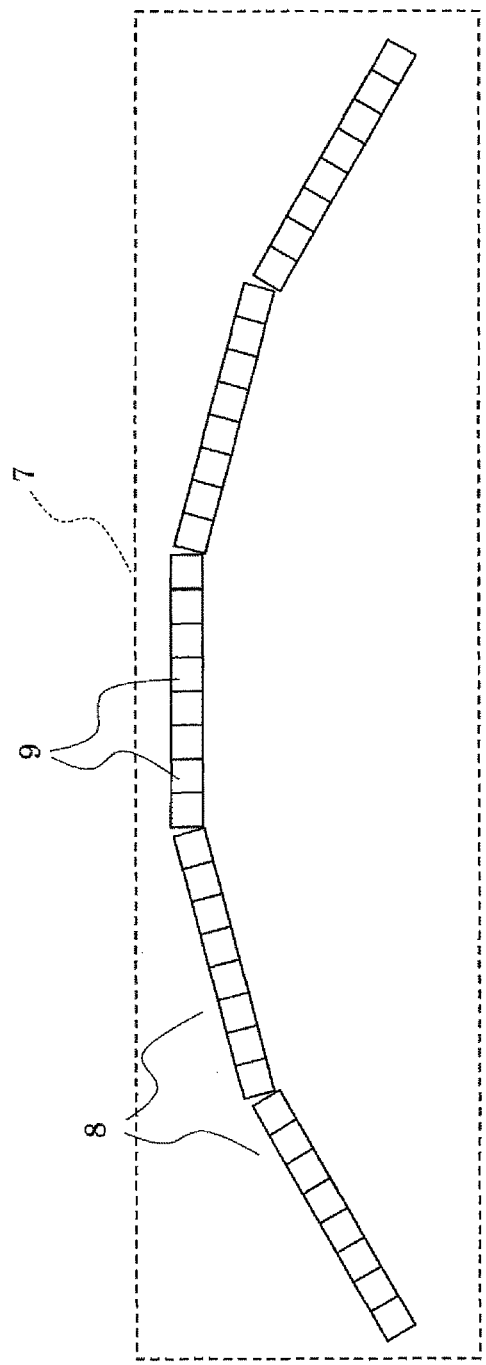
FIG. 2 is a diagram illustrating an exemplary configuration of a detector panel of the first embodiment of the present invention.

FIG. 2 is a diagram illustrating an exemplary configuration of the detector panel. The detector panel 7 is actually an array of detector modules 8 formed by a plurality of detector pixels 9 as illustrated in FIG. 2. The detector module 8 is arranged on an arc the center of which is the position of the X-ray tube 6. Although not illustrated, a collimator for removing scattered X-rays, which are X-rays scattered in the body of the subject 5, is attached to a surface of the detector module 8 facing the X-ray tube 6.

Figure 3:
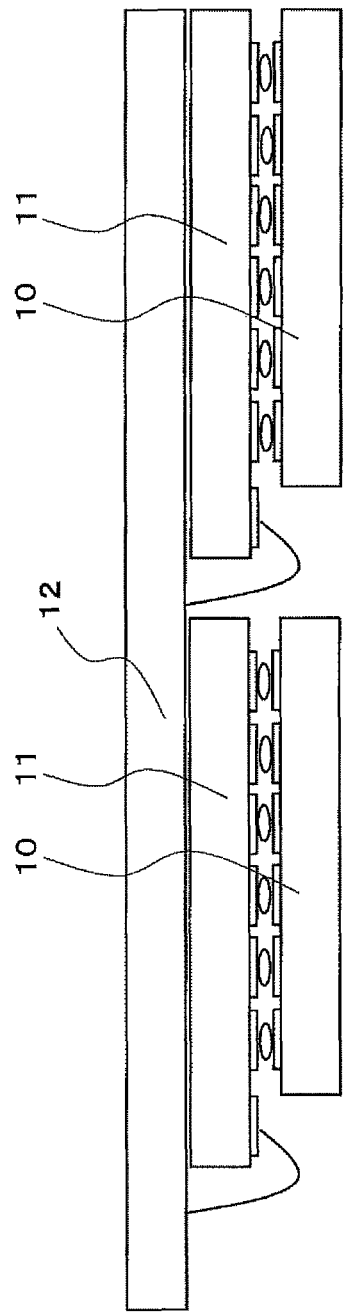
FIG. 3 is a diagram illustrating an exemplary configuration of a detector module of the first embodiment of the present invention.

A structure of the detector module 8 will be described with reference to FIG. 3. In the detector module 8, a plurality of application specific integrated circuits (ASICs) 11 are mounted on a holding substrate 12. The ASICs 11 are connected to the substrate by a bonding wire and thereby supplied of or controlled of power supply. On a surface of an ASIC 11, pads for connecting with a detector 10 are provided, and the detector 10 is connected thereto via the pads. An electrode pitch of the detector 10 is manufactured at the same pitch as an electrode pitch of the ASIC 11, and one detector pixel 9 is connected to one reading circuit 20 (see FIG. 4 to be described later). For connection between the ASIC 11 and the detector 10, solder, a conductive adhesive, or the like is used. In addition, in order to secure adhesive strength, a nonconductive adhesive such as underfill may be used at portions other than electrode portions. Note that the ASIC 11 corresponds to the "radiation counting apparatus" for counting X-rays (radiation) for image reconstruction. Furthermore, the reading circuit block 20 corresponds to a "measuring circuit".

The detector 10 is made of CdTe or CdZnTe like the one in the background art, and electrodes are formed on two opposing faces of a semiconductor element. For example, on one surface of the semiconductor element, an electrode is formed on the entire surface, and a high voltage is applied between opposing electrodes for collecting charges generated on the basis of interaction between X-rays and the semiconductor element. An electrode on the opposite surface of the semiconductor element is pixelated by patterning, which is, allowed to form each of the detector pixels 9 to read out a charge signal. Both electrodes are formed using gold or platinum. The length of a side of the detector is about 10 to 20 mm. When one pixel is 0.5 mm for a photon counting CT, 20 to 40 pixels are arranged in a row, which is arranged in a plane, and thus one element is formed with several hundreds to several thousands of pixels. Generally, a large number of detector pixels 9 each having a rectangular shape are arranged; however, it is also possible to arrange a plurality of elements of different sizes or to change the size of pixels in accordance with a grid position (the position of the collimator) for removal of scattered radiation, for example. The thickness of the element is sufficient to detect X-rays, and for medical apparatuses the thickness is about 2 mm.

It is preferable to allow the detector 10 to be larger than the ASIC 11 and to have a sufficient thickness to prevent radiation (X-rays) from hitting the ASIC 11 and to thereby prevent the ASIC 11 from being damaged by X-rays. Moreover, by providing a guard ring on an outer circumference portion of the detector 10, it is possible not only to prevent a leakage current on an element creeping surface from flowing to a detection circuit of the ASIC 11, but also to obtain an effect of bringing the element close to a parallel electric field. Note that in FIG. 3, for the convenience of drawing, the ASIC 11 is illustrated larger than the detector 10.

Figure 4:
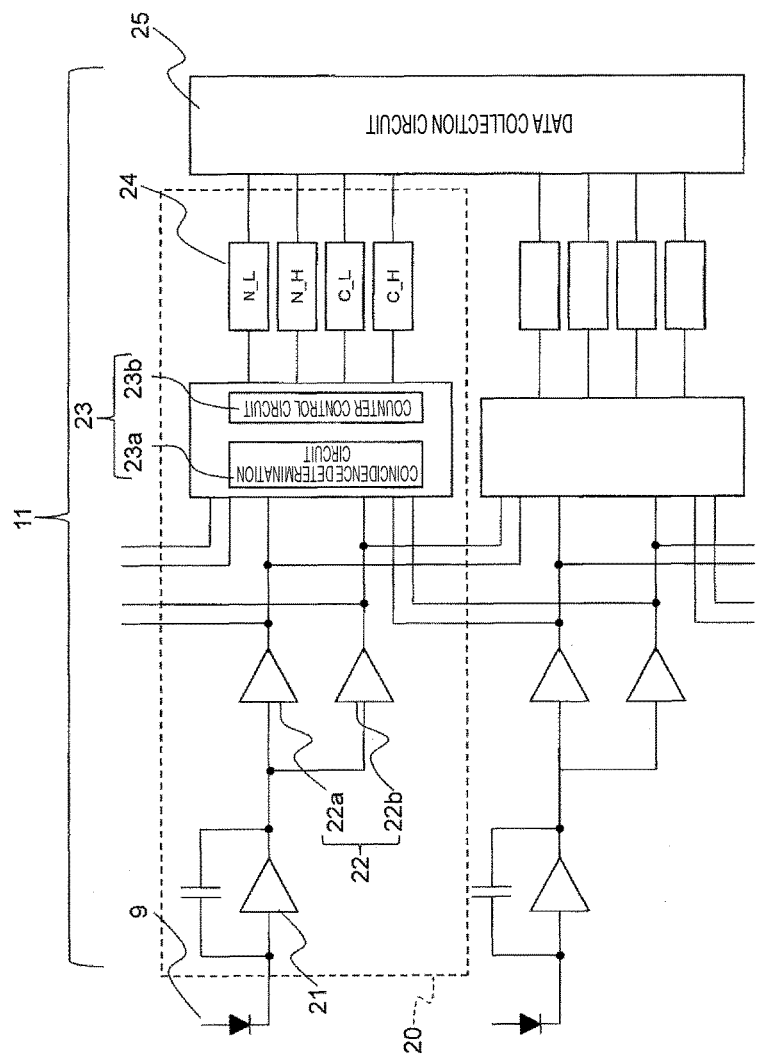
FIG. 4 is a diagram illustrating an exemplary configuration of a circuit of the first embodiment of the present invention.

A circuit of the ASIC 11 as a radiation counting apparatus will be described with reference to FIG. 4 illustrating an exemplary circuit configuration. The ASIC converts a charge of each of the detector pixels 9 generated by the detector 10 into an electric signal and collects data on the basis of the magnitude thereof. As illustrated in FIG. 4, the ASIC 11 includes a plurality of reading circuit blocks 20 and a data collection circuit 25. In the figure, although the reading circuit blocks 20 are arranged in only one row (they are one-dimensionally illustrated), actually, the reading circuit blocks 20 are arranged vertically and horizontally (arranged corresponding to an arrangement in FIG. 6 to be described later). Of course, it is preferable that the arrangement of the reading circuit blocks 20 coincide with a structure (arrangement) of the detector pixels 9 from the viewpoint of shortening and uniformizing the length of wiring. The arrangement of the reading circuit blocks 20 is also changed in accordance with the arrangement of the detector pixels 9. Incidentally, signal processing in the order of several nanoseconds is carried out in this embodiment as will be described later, and thus it is desirable to shorten the wiring and to make the length uniform. Note that, uniformizing the length means to make the distance of wiring between the detector pixel 9 and the reading circuit block 20 the same regardless of which combination of the detector pixel 9 and the reading circuit block 20.

The detector pixel 9 is connected to a charge amplifier 21 in the reading circuit block 20. The charge amplifier 21 converts a charge signal into a voltage signal using a feedback capacitance. Since the detector pixel 9 generates a charge proportional to the energy of reacted X-rays, an output wave height of the charge amplifier 21 is also proportional to the energy. Although not illustrated, in order to prevent charges from continuing to accumulate in the feedback capacitance, a switch for resetting the charge is provided, or charge accumulated by resistance is discharged.

An output of the charge amplifier 21 is connected to a plurality of comparators 22 (22a and 22b). The comparator 22a and the comparator 22b compare different voltages and generate a trigger signal when a threshold value is exceeded. By setting a threshold value of the comparator 22b high and a threshold of the comparator 22a low, a trigger is generated only in the comparator 22a when the energy is low, and when the energy is high both of the comparator 22a and the comparator 22b generate a trigger. Although two comparators are provided in the present embodiment, energy measurement may be performed using more comparators 22. In addition, as a method of measuring energy, a comparison in a digital circuit may be performed using an analog-to-digital converter (ADC) in order to obtain a count value for each energy window. By adjusting the threshold value, it is possible to count (count) X-ray events entering a specific energy window. Note that the comparators 22 correspond to an "energy measuring circuit" that measures energy when the detector pixel 9 detects X-rays (radiation).

An output of the comparators 22 is connected to a control circuit 23 including a coincidence determination circuit 23a and a counter control circuit 23b. In addition to the comparator 22 in the reading circuit block 20 to which the control circuit 23 belongs, the control circuit also receives outputs of comparators 22 in other adjacent reading circuit blocks 20 (range of "adjacent" will be described later with reference to FIG. 7). The control circuit 23 controls the counter 24 according to conditions of output of these comparators 22 and advances counting. A plurality of counters 24 is connected to the control circuit 23. For example, when there are two comparators in the reading circuit block 20, a total of four counters 24 are included as illustrated in FIG. 4 with two types of energy windows and a combination of coincidence counting and non-coincidence counting.

Specifically, in the example of FIG. 4, the comparators 22 includes the comparator 22a (low threshold value) and the comparator 22b (high threshold value) having different threshold values, and thus there are also two energy windows of high and low. That is, two out of the four counters 24 include a counter 24 having an energy window 1 (low energy) and a counter 24 having an energy window 2 (high energy) for non-coincidence counting. In FIG. 4, "N_L" (non-coincidence_low) and "N_H" (non-coincidence-_high) are written in frames of the counters 24. The remaining two are a counter 24 having an energy window (low energy) and a counter 24 having an energy window 2 (high energy) for coincidence counting. In FIG. 4, "C_L" (coincidence_low) and "C_H" (coincidence-_high) are written in frames of the counters 24. Note that "N" stands for non-coincidence and stands for coincidence. Incidentally, when the number of the comparators 22 in the reading circuit block 20 is increased to four, the number of the counters 24 is increased to eight. Note that, as described above, the control circuit 23 in this embodiment includes the coincidence determination circuit 23a that performs coincidence determination and the counter control circuit 23b that controls the counters 24.

The data collection circuit 25 transfers count values of the counters 24 to the data processing device 2 in response to an external control signal. A plurality of data collection circuits 25 is present in the apparatus. Therefore, data is transferred via a circuit (not illustrated) for arbitrating the plurality of data collection circuits 25. In addition, the data collection circuit 25 resets a value of the counters 24 after reading.

Figure 5:
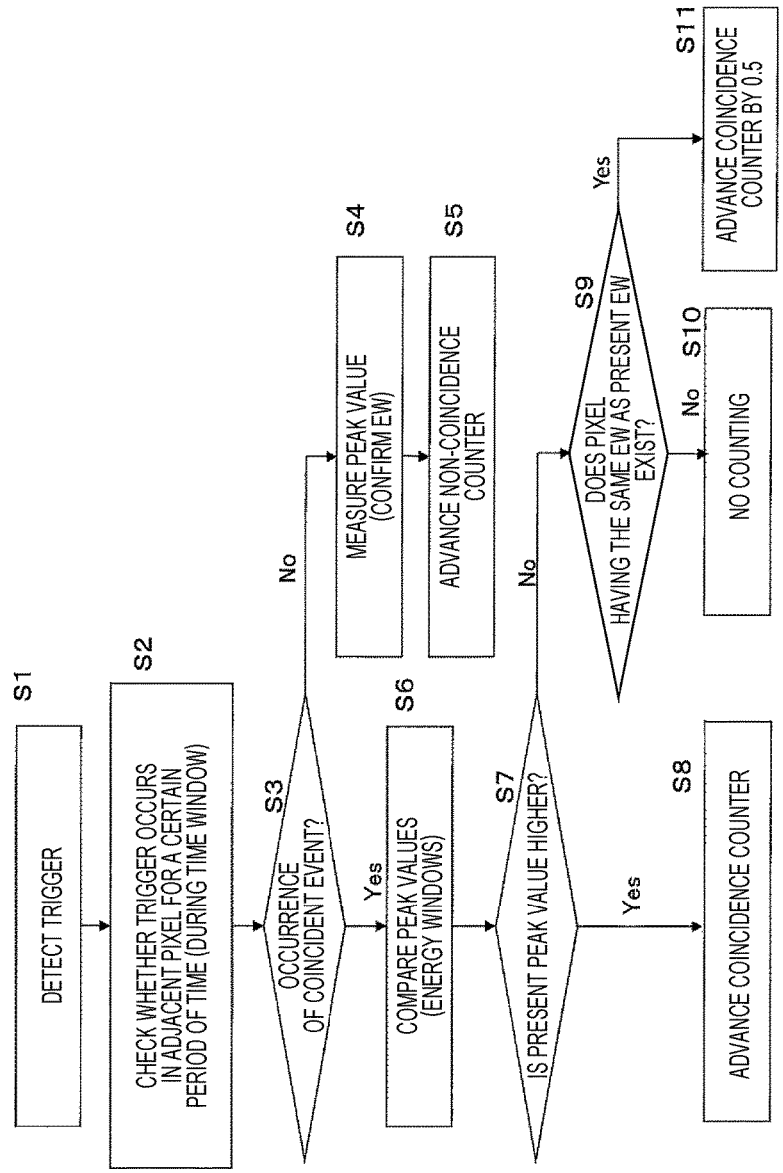
FIG. 5 is a diagram illustrating a determination flow of the first embodiment of the present invention.

FIG. 5 is a diagram illustrating a determination flow. Operations of the control circuit 23 of the first embodiment will be described with reference to FIG. 5. The control circuit 23 operates using an output of the comparator 22 in the reading circuit block 20 as a trigger (step S1). When receiving the trigger, the coincidence determination circuit 23a of the control circuit 23 checks whether a trigger is generated in adjacent channels (adjacent reading circuit blocks 20) for a certain period of time (during a time window), for example, for 5 nsec (step S2). Ensuring a certain period of time (time window) is because occurrence time of a trigger fluctuates depending on a generated charge amount or a position of charge generation. It is thus desirable to set the minimum time within the range of this fluctuation as determination time. When no coincidence event (trigger) occurs in the vicinity (step S3→No), the counter control circuit 23b of the control circuit 23 measures a peak value in the present reading circuit block 20 and confirms an energy window of a signal (Step S4). For this, a value of the one having the highest threshold value among the comparators 22a and 22b generating the trigger is used. In this manner, energy windows can be classified into the same number of energy windows as the number of comparators 22. Incidentally, in FIG. 5, an energy window is abbreviated as "EW".

Note that since the comparator 22a has a lower threshold value in the two comparators 22, the comparator 22a generates a trigger faster than the comparator 22b having a high threshold value. For this reason, in the present embodiment, an output of the comparator 22a is used as a trigger. Of course an output of the comparator 22b may be adopted as a trigger. When an output of the comparator 22b is used as a trigger, however, there are cases where the comparator 22a outputs while the comparator 22b does not output due to a difference in threshold value, and thus it is preferable to use an output of the comparator 22a as a trigger. Incidentally, the coincidence determination circuit 23a performs coincidence determination processing using an output of the comparator 22a as a trigger.

When the measured energy window is confirmed (step S4), the counter control circuit 23b adds 1 to the counter 24 having an energy window corresponding to the measured energy window. In this example, a counter 24 (N_L or N_H) for non-coincidence counting is advanced (step S5). For example, it is possible to measure that the energy window is 1 when only the low-threshold value comparator 22a generates a trigger and the high-threshold value comparator 22b does not generate a trigger. In this case, in step S5, addition is performed on the counter 24 having the energy window 1 (N_L) for non-coincidence counting (N_L→+1). If a trigger is generated also in the comparator 22b having a high threshold value, in step S5, addition is performed on the counter 24 having the energy window 2 (N_H) for non-coincidence counting (N_H→+1), but no addition is performed on the counter 24 having the energy window 1 (N_L).

If a trigger occurs in an adjacent channel (comparators 22 of a reading circuit block 20 of an adjacent detector pixel 9) within a certain period of time (for example within a time window of 5 nsec) during which determination of coincidence is made, since this is occurrence of a coincidence event (step S3→Yes), the counter control circuit 23b compares an energy window of the adjacent channel thereof (hereinafter referred to as "pixel" as appropriate) with the present energy window. That is, peak values are compared (step S6). If the present energy window is higher than an energy window of an adjacent pixel (step S7→Yes), a trigger generated in the adjacent pixel is considered to have been induced by an event of the present pixel. Therefore, a counter control circuit 23b of the pixel having the higher energy window controls the counter 24 connected thereto. Specifically, in step S8, the counter control circuit 23b advances the counter 24 corresponding to the coincidence energy windows, here, the counter 24 for coincidence counting having the energy window 2 by one (C_H→+1).

On the other hand, if there is no pixel having an energy window higher than the energy window of the present pixel among events generated in adjacent pixels (step S7→No), energy windows of the adjacent pixels are higher than that of the present pixel (step S9→No), or the energy windows of the adjacent pixels are the same as that of the present pixel (step S9→Yes).

When a peak value of an adjacent pixel is higher, that is, when there is no pixel having an energy window same as that of the present pixel (step S9→No), since the present trigger can be considered as an event induced by an event in an adjacent pixel (adjacent detector pixel 9). Therefore, the counter control circuit 23b does not advance any of the counters 24 connected thereto (step S10). On the other hand, if the energy window is the same as that of an adjacent pixel (step S9→Yes), the main source of the coincidence event cannot be specified. Therefore, the counter control circuit 23b advances the counters 24 for coincidence counting by 0.5 (step S11). Incidentally, when this step S9 is Yes (that is, when pixels having the same energy window are present), there are two cases of a case where the energy window (peak value) is the same low value (when both in the present pixel and the adjacent pixel only the comparator 22a outputs) and a case where the energy window (peak value) is the same high value (when both in the present pixel and the adjacent pixel the comparator 22a and the comparator 22b output). In the former case, 0.5 is added to the counter 24 for coincidence counting having the energy window 1 (C_L→+0.5), and in the latter case, 0.5 is added to the counter 24 for coincidence counting having the energy window 2 (C_H→+0.5). That is, upon controlling the operation of incrementing the counters 24, the counter control circuit 23b changes the increment amount of count values on the basis of the result of coincidence determination.

Note that, since the counter 24 of a digital circuit cannot actually count 0.5, a doubled value is entered in the counter 24 for coincidence counting, and by multiplying the count value by 0.5 in the last processing in which all counts have been completed, the final count value is acquired. Incidentally, although it is described that 1 (C_H→+1) is added to the counter 24 having the energy window 2 in step S8, a doubled value is entered also in step S8 in order to match with step S11. That is, in the case where there is a coincidence event (in the case of step S3→Yes), both of advancing of the counter 24 in step S8 and advancing of the counter 24 in step S11 are performed by a doubled value and then halved at the end.

Incidentally, the width of the time window described above is determined in consideration of the response characteristics of the detector 10 or the reading circuit block 20. In this example, the time window is set to 5 nsec as an example. When a time window is widened, the number of accidental coincidence counting tends to increase. Note that when the rate of incidence of radiation (X-rays) is increased, it is preferable that a time window is narrow since an accidental coincidence counting is reduced. However, when a time window is narrow, an influence of fluctuation in generation time of a trigger becomes large as described above. Considering these points, it is preferable to set a time window within a range of 3 to 10 nsec. The aforementioned time window value of 5 nsec is within the range of 3 to 10 nsec.

Figure 6:
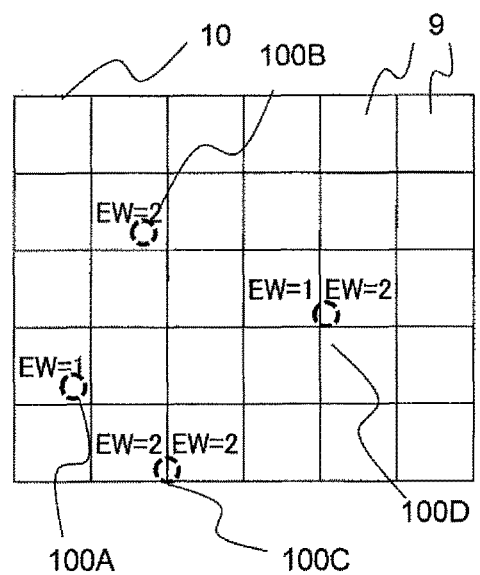
FIG. 6 is a diagram illustrating exemplary occurrence of events of the first embodiment of the present invention.

Next, an example of actual processing will be described with reference to FIGS. 6 and 7. FIG. 6 schematically illustrates a part of a state (lattice array) in which the detector pixels 9 are arranged on a plane. In the example in the figure, the detector 10 has six detector pixels 9 in the lateral direction and five detector pixels in the longitudinal direction, arranged in a lattice pattern. Since one detector pixel 9 corresponds to one pixel (and further to a reading circuit block 20), in the example of FIG. 6 (and FIG. 7), the detector 10 includes 30 pixels (=6×5 pixels) of detector pixels 9. In FIG. 6, four separate X-rays are incident and recorded as events in each pixel. Letters EW in the figure indicates an energy window, and the larger a numerical value indicated by "EW=" is, the higher energy is measured. For example, an X-ray event 100A generates a trigger of the energy window 1 (EW=1) in one pixel. An X-ray event 100B generates one event having the energy window 2 (EW=2), an X-ray event 100 C generates two events having the energy window 2 (EW=2) in, an X-ray event 100D generates an event having the energy window 2 (EW=2) in one pixel and an event having the energy window 1 (EW=1) in another pixel.

Figure 7:
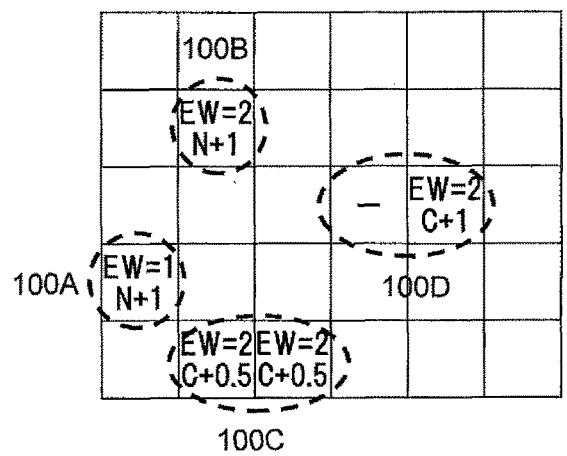
FIG. 7 is a diagram illustrating exemplary processing of events of the first embodiment of the present invention corresponding to FIG. 6.

FIG. 7 is a diagram illustrating the increment amount of each of the counters after processing corresponding to FIG. 6. Here, the term "adjacent" will be described. The term "adjacent" refers to, for example, a range including pixels subjected to coincidence measurement determination. In the present embodiment illustrated in FIGS. 6 and 7, adjacent pixels (detector pixels 9) are regarded as four pixels above, below, right and left of the present pixel. Since most of events due to scattering in a detector occur in adjacent pixels, it is desirable to judge four pixels sharing a side of the pixel. This is because as the number of pixels subjected to coincidence measurement determination increases, not only the circuit scale (the number of reading circuit blocks 20) increases, but also erroneous events are more likely to occur due to accidental coincidence counting and the like. Note that, when the detector pixel 9 is further miniaturized, it is desirable to broaden the range of "adjacent" to include 8 pixels including diagonal pixels or pixels two or three pixels apart.

In FIG. 7, (1) in the X-ray event 100A only an event of the energy window 1 of low energy is measured, and no event is measured in adjacent pixels. Therefore, the counter 24 for non-coincidence counting having the energy window 1 is incremented by 1 (N_L→+1). Note that in FIG. 7 it is described as "EW=1 N+1". (2) Similarly in the case of the X-ray event 100B, only an event of the energy window 2 of high energy is measured, and thus the counter for non-coincidence counting having the energy window 2 is incremented by 1 (N_H→+1). Note that in FIG. 7 it is described as "EW=2 N+1".

Also, (3) in an X-ray event 100C a signal is divided to two pixels. In a circuit (reading circuit block 20) of the left pixel, energy windows of the left and the right pixels are compared, and since only an event of the same level of energy exists, the counter for coincidence counting is incremented by 0.5 (C—H→+0.5). Note that in FIG. 7 it is described as "EW=2 C+0.5". Meanwhile, similar processing is performed also in a circuit (reading circuit block 20) of the right pixel. Also in the right pixel comparison with adjacent pixels is performed, and in this case the coincidence counter is incremented by 0.5 (C_H→+0.5) since the right pixel has an event of the same energy window as that of the left pixel. Note that in FIG. 7 it is described as "EW=2 C+0.5". (4) In the case of an X-ray event 100D, in the left pixel energy windows of the left and the right pixels are compared, and since the energy window of the right pixel is high, the counter 24 for coincidence counting is not incremented in the left pixel. Note that in FIG. 7 it is described as "-". On the other hand in the right pixel, since its own energy window is high, the counter 24 for coincidence counting having the energy window 2 of its own is incremented by 1 (C_H→+1). Note that in FIG. 7 it is described as "EW=2 C+1".

As described above in the first embodiment, processing is performed while conditional branching of adjacent pixels is performed independently. This allows an event, which is counted as two in simple counting, to be counted as one. In addition, since only the higher energy is used, erroneous detection due to induced charge can be avoided. Of course one X-ray event may be measured across three or more pixels, but if it is divided to three or more pixels, a peak value (energy window) of each pixel drops and possibility of exceeding the threshold value is low, which is a few percentages or less of the entire proportion, processing by this processing method does not cause a big problem.

In this manner, information on the number of X-rays incident on the detector panel 7 within a certain period of time can be acquired. The data processing device 2 performs image reconstruction using the above data. Data obtained from the detector panel 7 includes two types of data in which counts for each of the energy windows have reacted in one detector pixel 9 and thus no coincidence counting has occurred (non-coincidence counting) and data in which counts for each of the energy windows have divided to two or more detector pixels 9 and have detected as coincidence counting (coincidence counting). Of these, a count value of non-coincidence counting with no coincidence counting is based on true energy and is used as primary data in image reconstruction.

On the other hand, energy is not accurate for a count of the coincidence counting while shifted to lower energy. How an energy spectrum of an event causing coincidence counting changes when X rays having a specific energy spectrum are incident is measure in advance for correcting a count value of coincidence counting on the basis of this data. By adding this corrected data to the count value of non-coincidence counting, it is possible to acquire data with high statistical accuracy while measurement errors are suppressed. In addition, when two pixels have high and low energy in coincidence counting, it is assumed that the X-ray is incident on a pixel (detector pixel 9) having higher energy and an incident position is thereby assumed. Values of the both pixels may be added for the energy, and a location where the event has occurred and the energy of the event may be thereby determined.

Moreover, for example, a count value obtained by summing both count values of coincidence counting and non-coincidence counting is obtained for each pixel, and at the time of this summing, different weights are used for the count value of coincidence counting and the count value of non-coincidence counting. As described above, since the count value of non-coincidence counting is based on true energy, when a weight for multiplying the count value of non-coincidence counting is 1, a weight for multiplying the count value of coincidence counting is a value less than 1. Then, image reconstruction is performed on the basis of the summed count value (that is, a value obtained by correcting the count value of non-coincidence counting). Incidentally, without multiplying the count value of coincidence counting by a weight less than 1, the count value of non-coincidence counting may be multiplied by a weight larger than 1. Note that multiplying the count of coincidence counting by a weight less than 1 means the same as adding a weight to the count value of a counter for non-coincidence counting.

As described above, the first embodiment includes the coincidence determination circuit 23a for determining, when incrementing a count value of the detector pixel 9, whether X-rays (radiation) has been coincidentally detected in other detector pixels 9 adjacent to the detector pixel 9, and the counter control circuit 23b switches the counter 24 for counting radiation on the basis of the determination result between non-coincidence use and coincidence use. Typically, the count value of the non-coincidence counter 24 is primarily used as the data for image reconstruction after correcting the counter value of the counter for coincidence use. According to the photon counting X-ray CT apparatus S of the present embodiment, it is possible to preferably cope with miniaturization of the detector pixels 9, and it is also possible to reduce circuit dead time. It is also possible to reduce power consumption per circuit. It is further possible to appropriately handle phenomena in which energy is detected while divided to a plurality of detector pixels 9 due to characteristic X-ray generation, Compton scattering or the like, charge sharing in which an electron cloud generated by X-rays spreads over two detector pixels 9, induced charges, and the like.

Second Embodiment

Next, a second embodiment will be described with reference to FIG. 8. The second embodiment is different from the first embodiment in that a coincidence determination circuit 23a is included outside a reading circuit block 20. That is, in the first embodiment, coincidence determination is performed by the coincidence determination circuit 23a in each reading circuit block 20 (for example, in the control circuit 23). In the present embodiment, however, coincidence determination is performed by the coincidence determination circuit 23a placed outside the reading circuit block 20.

That is, the reading circuit block 20 includes a charge amplifier 21, comparators 22 (energy measuring circuit), counters 24, and a counter control circuit 23b. The reading circuit block 20 is provided to each detector pixel 9. The coincidence determination circuit 23a is disposed between pixels (between reading circuit blocks 20) and is connected to each of comparators 22 of the two (multiple) pixels (reading circuit blocks 20). The coincidence determination circuit 23a is also connected to counter control circuits 23b in reading circuit blocks 20 including the comparators 22 connected thereto. The coincidence determination circuit 23a transfers, to the counter control circuit 23b, information on whether an event has occurred coincidentally in two detector pixels 9 within a certain period of time (within a time window) and information on whether an energy window is equal, larger, or smaller. The counter control circuit 23b controls the counters 24 on the basis of signals from the plurality of coincidence determination circuits 23a. In the present embodiment, coincidence determination between two (multiple) pixels is performed by one circuit, and thus the circuit scale can be reduced as compared to the configuration of the first embodiment performing coincidence determination individually. Moreover, it is possible to avoid a problem that determination in coincidence determination differs depending on an error in the time window.

Third Embodiment

A third embodiment will be described with reference to FIG. 9. In the third embodiment, in addition to a counter 27 connected to a coincidence determination circuit 23a, that the number of types of counters 24 connected to the counter control circuit 23b is increased are different points from the first and the second embodiments. In the X-ray CT apparatus S, the number of X-rays detected by the detector pixels 9 is very large, and it is necessary to process events of several tens to several hundred Mcps. When coincidence determination is performed under such a high counting rate, not only one X-ray divided into two (not only those illustrated in FIG. 6 and FIG. 7) but also a phenomenon called accidental coincidence counting in which coincidence detection is accidentally made occur.

The present embodiment is different from the first and the second embodiments in that a means for correcting accidental coincidence counting is provided. When accidental coincidence counting occurs, the original two events are measured as one event. In the present embodiment, simple counters (counters for simple counting) for incrementing a count regardless of coincidence or non-coincidence are added to the counters 24 controlled by the counter control circuit 23b. In image reconstruction, it is possible to estimate a correct energy spectrum and a counting rate by calculating count values of the counters of coincidence counting, the counters 24 of non-coincidence counting, and the counters 24 of simple counting with the energy spectrum and the counting rate using as parameters and by performing inverse calculation thereof.

Incidentally, in FIG. 9, those simply indicated as "L" and "H" in a frame are the simple counters 24. Contrarily to that the other counters 24 (the counters 24 for non-coincidence counting and the counters 24 of coincidence counting) add a value to either ones according to a result of coincidence determination, the counters 24 for simple counting simply increments a value without referring to the result of coincidence determination.

As illustrated in FIG. 9, in the present embodiment, a counter for coincidence counting is also connected to the coincidence determination circuit 23a as a counter 27. This counter 27 for coincidence counting counts coincidence events between pixels. To supplement, the counter 27 for coincidence counting is provided for each combination of reading circuit blocks 20 (for each combination of detector pixels 9). Note that, although not illustrated, this counter 27 includes three types of counters for each energy window, a total of three counters including two counters for counting when an energy window of one pixel is higher than that of another and one counter for counting when both energy windows are equal. That is, the counter 27 includes a counter for each of the cases where, in one pixel and the other pixel, the one is higher, the both are equal, and the one is lower.

Note that, in order to remove scattered radiation generated in the body of the subject 5, an X-ray CT includes a collimator for blocking X-rays incident on detector pixels 9 from an oblique direction. In the collimator, slits are formed of a substance having a high stopping power of X-rays such as tungsten. Due to this collimator for removing scattered radiation, a region not irradiated with X rays is partially generated in a detector. In the present embodiment, the collimator is arranged such that the positions not irradiated with X-rays coincide with boundaries between pixels (between the detector pixels 9). Since a pixel pitch is finer than a spacing of slits, two to four pixels of detector pixels 9 are placed within a slit. It is desirable that the interval between slits and the pitch of the detector pixels 9 have a ration of an integral multiple. In a shadow portion of the collimator, a ratio of events divided into two events due to reduced X-rays reacting at a boundary of pixels decreases as compared to a portion not shaded by the collimator. In the present embodiment, a ratio of accidental coincidence counting is estimated by using count values of pixels including the shadow portion of the collimator and pixels not including the shadow portion, and a true count value is thereby obtained. Image reconstruction is performed from this true count value. That is, out of counters 24 (27) of coincidence counting, a count for a shadow portion of the collimator and a count for the other portion are counted separately and an error in a counting rate is thereby corrected.

Incidentally, in FIG. 6 (FIG. 7), as an example, the detector 10 in which detector pixels 9 are arranged in a 5×6 matrix is illustrated. Each of the detector pixels 9 is provided an address to allow unique identification of each position. It is further possible to specify which detector pixel 9 is shaded by the collimator out of the respective detector pixels 9.

Note that, although FIG. 9 illustrates an example in which six counters 24 are connected to the counter control circuit 23b, the counter control circuit 23b may be connected to four counters 24 (two counters 24 for non-coincidence counting and two counters 24 for simple counting) while the coincidence determination circuit 23a may be connected to a predetermined number of counters 27 for coincidence counting.

<Miscellaneous 1>

In the embodiment described above, in the case where one X-ray event is disadvantageously measured (divided and measured) across three or more pixels due to scattering or the like in the detector 10 (detector pixel 9), processing for such an X-ray event is omitted since a peak value at each pixel decreases (that is, an energy window decreases) in such a case. In other words, on the premise that coincidence determination by the coincidence determination circuit 23a is coincidence in two pixels, the counter control circuit 23b adds 0.5 to the counter 24 for coincidence counting in the case of coincidence determination that another pixel having the same energy window as that of the present pixel exists in the vicinity thereof (in the case of step S9→Yes). However, when the size of pixels is further miniaturized, the number of times one X-ray event is measured across three or more pixels is considered to increase. In this case, the number of pixels determined to be coincident by the coincidence determination circuit 23a (the number of pixels determined to be coincident) is calculated, and the counter control circuit 23b controls the counters 24 for coincidence counting such that a count value to be added corresponds to the number of pixels determined to be coincident. Specifically, in the flow chart of FIG. 5, if there is one pixel having the same energy window as that of the present pixel adjacent thereto (if there are two pixels including the present pixel) (see step S9), ½=0.5 is added to the counters 24 for coincidence counting in step S11. Meanwhile, if there are two pixels having the same energy window as that of the present pixel adjacent thereto (if there are three pixels including the present pixel) (see step S9), ⅓=0.33 is added to the counters 24 for coincidence counting in step S11.

That is, the counter control circuit 23b adds a count value corresponding to the number of pixels determined to be coincident (the number of pixels having the same energy window) to the counters 24 for coincidence counting. In other words, the counter control circuit 23b changes the increment amount of a count value in the counter 24 on the basis of the determination result of the coincidence determination circuit 23a. Further in other words, the counter control circuit 23b calculates the increment amount of a count value from a weight obtained as a reciprocal of the number of pixels determined to be coincident (the number of pixels having the same energy window). Note that, as described above, when one X-ray event is disadvantageously measured across three or more pixels, an energy window (peak value) at each pixel decreases. For this reason, such coincidence determination processing may be preferably performed by further increasing the number of comparators 22 and further dividing energy windows (in the above embodiment, there are two types of energy windows: high and low).

Incidentally, when the counter 24 adds an integer value, for example, it is only required to multiply the increment amount of the count value by 100 for the addition and to divide by 100 in the end. For example, it is only required to add 50 to the counters 24 for coincidence determination when an increment amount of a count value is 0.5 and to add 33 to the counters 24 for coincidence determination when an increment amount of a count value is 0.33, and to divide by 100 in the end. Note that, when such processing is performed, with respect to the range of "adjacent", it is desirable to broaden the range of "adjacent" to include 8 pixels including diagonal pixels or pixels two or three pixels apart. Note that, when the range of adjacent is broadened in the above manner, the coincidence determination circuit 23a is connected to comparators 22 (22a and 22b) of pixels belonging to the broadened range of adjacent (see FIG. 4).

<Miscellaneous 2>

The present invention described above is not limited to only the embodiments (the first to the third embodiments) described above, but various variations are included within the scope of achieving essential effects of the invention. For example, the aforementioned embodiments are described in detail in order to facilitate understanding of the present invention and thus the present invention is not necessarily limited to include all of the configurations having been described. Naturally, a part of a configuration of one of the embodiments may be replaced with a configuration of another embodiment. Also naturally, a configuration of one of the embodiments may be added with a configuration of another embodiment. Moreover, a part of a configuration of each of the embodiments may be added with, deleted of, or replaced with another configuration.

In the respective embodiments, only control lines or data lines that are considered necessary for the purpose of description are illustrated and thus all of control lines or data lines in a product are not always illustrated. In fact, it can be assumed that substantially all of the configurations are connected with each other. Moreover, each processing may be performed by hardware or software. Furthermore, the present invention may be applied to detection of gamma rays. For example, the present invention may be applied to detect (count) radiation (gamma rays) emitted from the body of the subject 5 by a radioactive agent (that is, to a nuclear medicine diagnosis apparatus).

REFERENCE SIGNS LIST

S X-ray CT apparatus (radiation imaging apparatus)
1 gantry
2 data processing device
3 image display device
4 bed
5 subject
6 X-ray tube
7 detector panel
8 detector module
9 detector pixel
10 detector (radiation detector)
11 ASIC (radiation counting apparatus)
12 holding substrate
20 reading circuit block (measuring circuit)
21 charge amplifier
22 comparator (measuring circuit)
22a (low-threshold value) comparator
22b (high-threshold value) comparator
23 control circuit
23a coincidence determination circuit
23b counter control circuit
24 counter
25 data collection circuit
27 counter (third embodiment)
100A, 100B, 100C, 100D X-ray event

The invention claimed is:

1. A radiation imaging apparatus, comprising:
a radiation detector comprising a plurality of detector pixels for detecting radiation;
an energy measuring circuit for measuring energy when one of the detector pixels detects radiation on the basis of a signal output by the radiation detector;
a plurality of counters for counting the number of detected radiations;
a coincidence determination circuit for determining whether radiation has been coincidentally detected at other detector pixels adjacent to the one detector pixel upon detection of the radiation;
a counter control circuit for controlling operation of incrementing one of the counters on the basis of the coincidence determination in the coincidence determination circuit and the energy in the energy measuring circuit; and
a data processing device for performing image reconstruction using values of the counters,
wherein the plurality of counters includes a counter for coincidence counting and a counter for non-coincidence counting with respect to the other adjacent detector pixels for each class of energy and performs image reconstruction on the basis of a count value of each of the counters.

2. The radiation imaging apparatus according to claim 1, wherein the energy measuring circuit, the counters, and the counter control circuit form reading circuit blocks corresponding to each of the detector pixels, and
the radiation imaging apparatus comprises the coincidence determination circuit that performs coincidence determination between adjacent reading circuit blocks.

3. The radiation imaging apparatus according to claim 2, wherein a counter for coincidence counting is provided for each combination of the reading circuit blocks.

4. The radiation imaging apparatus according to claim 3, wherein, out of counters of coincidence counting, a count for a shadow portion of a collimator and a count for the other portion are counted separately and an error in a counting rate is corrected.

5. The radiation imaging apparatus according to claim 1, wherein the detector pixels are two-dimensionally arranged.

6. The radiation imaging apparatus according to claim 5, wherein a measuring circuit is configured by including the energy measuring circuit, the coincidence determination circuit, the counter control circuit, and a charge amplifier connected to one of the detector pixels, and the measuring circuit performs determination with other four measuring circuits adjacent thereto as the other adjacent detector pixels.

7. The radiation imaging apparatus according to claim 1, wherein the counter control circuit changes an increment amount of a count value when controlling operation of incrementing the counters on the basis of a result of the coincidence determination.

8. The radiation imaging apparatus according to claim 1, wherein the counter control circuit calculates an increment amount of a count value when controlling operation of incrementing the counters from a weight obtained as a reciprocal of the number of detector pixels determined as being coincident by the coincidence determination circuit.

9. The radiation imaging apparatus according to claim 1, wherein the energy measuring circuit comprises a plurality of comparators having different threshold values, and
the coincidence determination circuit starts the determination as to whether coincident or not using an output of one of the comparators having the lowest threshold value as a trigger.

10. The radiation imaging apparatus according to claim 1, wherein, upon performing image reconstruction on the basis of a count value of each of the counters,
a count value of the counter for coincidence counting is multiplied by a weight of a value less than 1, and the sum of the multiplied count value and a count value of the counter for non-coincidence counting are calculated to correct the count value of the counter for non-coincidence counting.

11. A radiation imaging apparatus, comprising:
a radiation detector comprising a plurality of detector pixels for detecting radiation;
an enemy measuring circuit for measuring energy when one of the detector pixels detects radiation on the basis of a signal output by the radiation detector;
a plurality of counters for counting the number of detected radiations;
a coincidence determination circuit for determining whether radiation has been coincidentally detected at other detector pixels adjacent to the one detector pixel upon detection of the radiation;
a counter control circuit for controlling operation of incrementing one of the counters on the basis of the coincidence determination in the coincidence determination circuit and the energy in the energy measuring circuit; and
a data processing device for performing image reconstruction using values of the counters,
wherein the plurality of counters includes three counters including a counter for coincidence counting, a counter for non-coincidence counting with respect to the other adjacent detector pixels and a counter for counting regardless of coincidence or non-coincidence for each class of energy and performs image reconstruction on the basis of a count value of each of the counters.

12. A radiation imaging method in a radiation imaging apparatus comprising:
a radiation detector comprising a plurality of detector pixels for detecting radiation;
an energy measuring circuit for measuring energy when one of the detector pixels detects radiation on the basis of a signal output by the radiation detector;
a plurality of counters for counting the number of detected radiations;
a coincidence determination circuit for determining whether radiation has been coincidentally detected at other detector pixels adjacent to the detector pixel upon detection of the radiation;
a counter control circuit for controlling operation of incrementing one of the counters; and
a data processing device for performing image reconstruction using a value of the counter,
wherein, on the basis of a result of coincidence determination in the coincidence determination circuit, the counter control circuit increments a count value of a counter for non-coincidence counting out of the plurality of counters when no coincidence is determined and increments a value of a count value of a counter for coincidence counting out of the plurality of counters when coincidence is determined.

13. The radiation imaging method according to claim 12, wherein, upon incrementing the count value, the counter control circuit adjusts an increment amount such that an increment amount of a count value of coincidence counting is smaller than an increment amount of a count value of non-coincidence counting.

* * * * *